United States Patent [19]

Katayama et al.

[11] 4,156,675
[45] May 29, 1979

[54] UREA POLYMER CONTAINING A SULFONATE RADICAL AND METHOD OF PREPARING THE SAME BY A POLYMERIZATION REACTION OF DIAMINOSULFONATE WITH DIISOCYANATE

[75] Inventors: Shitomi Katayama; Takeyasu Iwashita, both of Yokohama; Kiyoshi Jin, Shiki, all of Japan

[73] Assignee: NHK Spring Co., Ltd., Yokohama, Japan

[21] Appl. No.: 878,865

[22] Filed: Feb. 17, 1978

[30] Foreign Application Priority Data

Feb. 25, 1977 [JP] Japan .................................. 52/19980

[51] Int. Cl.$^2$ ............................................. C08G 18/38
[52] U.S. Cl. ...................................... 260/37 N; 528/68
[58] Field of Search ................... 260/77.5 CH, 37 N; 528/68

[56] References Cited

U.S. PATENT DOCUMENTS

| 3,687,902 | 8/1972 | Perrino et al. ............... 260/77.5 CH |
| 3,870,684 | 3/1975 | Witt et al. ..................... 260/77.5 CH |
| 3,970,599 | 7/1976 | Schwarcz et al. ........... 260/77.5 CH |

*Primary Examiner*—Maurice J. Welsh

[57] ABSTRACT

A urea compound having a sulfonate radical is obtained by reaction of aminoaminosulfonate represented by the formula:

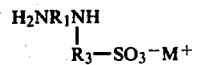

(where $R_1$ is a hydrocarbon-based radical, and $R_3$ is propylene radical, a substituted propylene radical, butylene radical or a substituted butylene radical) with diisocyanate, optionally in the presence of diamine and/or water. The reaction may be achieved by interfacial polymerization, solution polymerization, or solvent-free polymerization.

51 Claims, No Drawings

UREA POLYMER CONTAINING A SULFONATE RADICAL, AND METHOD OF PREPARING THE SAME BY A POLYMERIZATION REACTION OF DIAMINOSULFONATE WITH DIISOCYANATE

BACKGROUND OF THE INVENTION

I. Field of the Invention:

This invention relates to a new electrolyte compound and a method for preparing the same, and more specifically to a urea compound having a sulfonate radical and a method for preparing the same. (The "urea compound having a sulfonate radical" may herein be alternatively referred to as "sulfonate urea compound".)

II. Description of the Prior Art:

Many synthetic high molecular-weight substances are defective in moisture-absorptive property, antistatic property, dyeability, etc., so that there have conventionally been used additives such as plasticizers or surface active agents for the improvement of such properties thereof. These ways of improvement have, however, been accompanied by several shortcomings, such as the additive's degradation with time, phase separation, etc. Therefore, it is most preferred to independently polymerize or copolymerize moisture- or water-absorptive monomers. However, in carrying out polyaddition or polycondensation, a full attention should be paid to the selections of raw materials and polymerization method, because a moisture- or water-absorptive functional group contained in some kind of the raw materials may give rise to the inhibition or prohibition of polymerization due to the effect of polarity of the functional group, or may be consumed and dissipated during the polymerization reaction.

SUMMARY OF THE INVENTION

An object of this invention is to provide a sulfonate urea compound having many advantages over the conventional high molecular-weight substances with respect to such properties as water-solubility, hydrophilic property, water-absorptive property, and antistatic property.

Other object of this invention is to provide a method for producing such sulfonate urea compound.

The urea compound having sulfonate radical of the invention may generally be represented by the general formula:

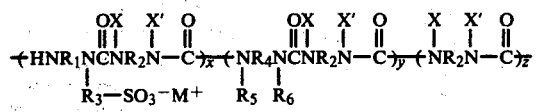

where $R_1$ is a divalent hydrocarbon-based radical having 2 to 17 carbon atoms, $R_2$ is a divalent hydrocarbon-based radical having 4 to 29 carbon atoms or polyether or polyester having an average molecular weight of 10,000 or less, $R_3$ is

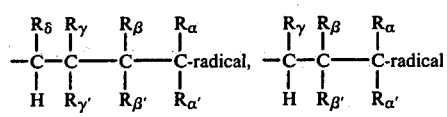

(wherein $R_\alpha$; $R_{\alpha'}$; $R_\beta$; $R_{\beta'}$; $R_\gamma$; $R_{\gamma'}$ and $R_{67}$ are independently hydrogen atom, alkyl radicals having 1 to 5 carbon atoms or any other monovalent radical unreactive with isocyanato or amino radicals), $R_4$ is a divalent hydrocarbon-based radical having 2 to 17 carbon atoms, or a radical which forms with adjacent nitrogens a piperidine or piperazine ring structure, $R_5$ and $R_6$ are independently a monovalent hydrocarbon-based radical having 1 to 16 carbon atoms or a divalent hydrocarbon-based radical to form together by mutual bond a carbon chain, X and X' are hydrogen atom or

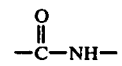

radicals representing amide bonds, $M^+$ is a cation, and x, y and z are values indicating the relative molar proportions of the respective units and complying with the required normalization: $x+y+z=1$; $0.1 \leq 100x/(x+y+z) \leq 100$; and $0 \leq 100z/x+y+z \leq 50$.

The sulfonate urea compound as given by the aforesaid general formula may be classified into four types as follows:

(1) Where $y=0$ and $z=0$, that is, component x alone is present;

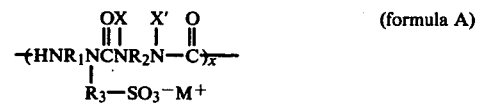

(2) Where $z=0$, that is, components x and y are present;

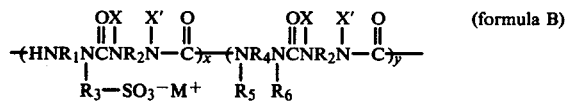

(3) Where $y=0$, that is, components x and z are present;

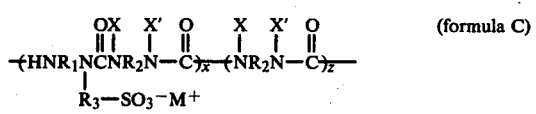

(4) Where components x, y and z are all present;

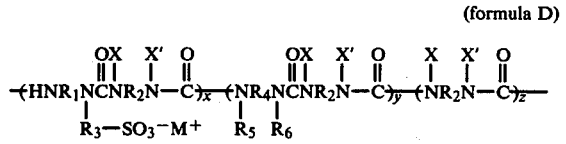

Each of general formulae (A) to (D) merely indicates a general structure of the composition of the constituents or of each unit, and is not intended to define the arrangements of the unit structures.

DETAILED DESCRIPTION OF THE PREFERRED EMBODIMENTS

"Hydrocarbon-based radical" as mentioned herein and in the appended claims is a generic expression of hydrocarbon radicals (aliphatic, alicyclic, aliphatic-substituted alicyclic, aromatic, aliphatic-substituted aromatic, alicyclic-substituted aromatic, and aliphatic-substituted alicyclic-substituted aromatic radicals) and substituted hydrocarbon radicals substituted with non-hydrocarbon groups (e.g., halogen, cyano group, etc.) which do not react with other starting materials and not inhibit or prohibit the intended reaction.

In the above formulae, $R_1$ represents a divalent radical derived from the elimination of two amino radicals from primary diamines known in the art. Such diamines include aliphatic diamines having 2 to 17 carbon atoms such as ethylenediamine, propylenediamine-(1,3), propylenediamine-(1,2), tetramethylenediamine, hexamethylenediamine, octamethylenediamine, heptadecamethylenediamine, 2,2,4-trimethylhexamethylenediamine and the like; alicyclic or aliphatic-substituted alicyclic diamine having 6 to 15 carbon atoms such as 1,3-diaminocyclohexane, 1,4-diaminocyclohexane, 1,3-diamino-1-methylcyclohexane, 3,5-diamino-1,1¹-dimethylcyclohexane, 1,5-diamino-1,3-dimethylcyclohexane, 3,1¹-diamino-1-methoxyethylcyclopentane, 1,5-diamino-1-methyl-3-methoethylcyclohexane, 1,4¹-diamino-1-methyl-4-methoethylcyclohexane, 1¹,3²-diamino-1-methyl-3-dimethoethylcyclopentane, 4,4'-diaminodicyclohexylmethane and the like; aromatic or aliphatic- and/or aliphatic-substituted aromatic diamines such as m-phenylenediamine, p-phenylenediamine, 4-methylphenylenediamine-(1,3), 2-methylphenylenediamine-(1,3), 3-aminobenzylamine, 4-aminobenzylamine, 4-amino-β-phenethylamine, p-xylylenediamine, 4,4'-diaminodiphenylmethane, 3,3'-dichloro-4,4'-diaminodiphenylmethane. Further, $R_1$ may contain any of functional groups which do not react with either amine or isocyanato groups nor retard or inhibit the polymerization reaction thereof. Examples of diamines containing such $R_1$ groups are halogen-substituted aromatic diamine, oxadialkylene-substituted diamines, ω,ω'-diamino-polyether and ω,ω'-diamino-polyester, the latter two polymer diamines having a repeating unit of 2 to 20 carbon atoms and an average molecular weight of 10,000 or less and preferably 10⁴ or more.

$R_2$ is a residual divalent radical of diisocyanate eliminated of the two isocyanato radicals. Such diisocyanates include aliphatic diisocyanates having 4 to 16 carbon atoms such as butane-1,4-diisocyanate, hexane-1,6-diisocyanate, nonane-1,9-diisocyanate, 2-methylbutane-1,4-diisocyanate, dimethylsilanediisocyanate and the like; alicyclic diisocyanates having 8 to 20 carbon atoms such as cyclohexane-1,3-diisocyanate, cyclohexane-1,4-diisocyanate, 1-ethylcyclohexane-2,4-diisocyanate, dicyclohexylmethane-4,4'-diisocyanate, ω,ω'-1,4-dimethylcyclohexanediisocyanate and the like; aliphatic-substituted aromatic diisocyanates having 9 to 20 carbon atoms such as 4-phenylisocyanatemethylisocyanate, 4-phenylisocyanate-β-ethylisocyanate and the like; alicyclic-substituted aromatic diisocyanates having 12 to 20 carbon atoms such as tetrahydronaphthylene-1,5-diisocyanate, hexahydrodiphenylmethane-4,4'-diisocyanate and the like; and aromatic diisocyanates having 8 to 29 carbon atoms such as 1,3-phenylenediisocyanate, 1,4-phenylenediisocyanate, 2,4-tolylenediisocyanate, 2,6-tolylenediisocyanate, naphthalene-2,7-diisocyanate, diphenylmethane-4,4'-diisocyanate and the like. In addition, isocyanato-terminated polyethers and polyesters having an average molecular weight of 10,000 or less and preferably 302 or more by a well known technique are also included.

Examples of $R_3$ are propylene, α-methylpropylene, α,α'-dimethylpropylene, β-methylpropylene, α,α,γ-trimethylpropylene, γ-methylpropylene, γ-n-pentylpropylene, butylene, α-methylbutylene, β-methylbutylene, δ-methylbutylene and β,δ-dimethylbutylene.

These groups for $R_3$ may further contain isocyanate radicals or monovalent radicals which are unreactive with amino radicals (for example, halogen, alkoxy, acyl, carboxyl, cyano, nitro or carbonyl group).

$R_4$, $R_5$ and $R_6$ are residual radicals derived from the elimination of the amino radicals from the diamines represented by the formula:

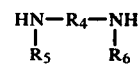

Such diamines include, in addition to the diamines exemplified for $R_1$, aliphatic secondary and mixed primary-secondary diamines having 3 to 28 carbon atoms such as N-methylethylenediamine, N-ethylethylenediamine, N-propylethylenediamine, N-methyltetramethylenediamine, N-(δ-chlorobutyl)pentamethylenediamine, N-methylhexamethylenediamine, N-ethylhexamethylenediamine, N-propylhexamethylenediamine, N-isobutylhexamethylenediamine, N,N'-dimethylethylenediamine, N,N'-diethylethylenediamine, N,N'-dimethyltetramethylenediamine, N,N'-dimethylhexamethylenediamine, N,N'-diethylhexamethylenediamine, 1,10-bis-octylamino-2,9-dimethyldecane and the like; alicyclic secondary and mixed primary-secondary diamines having 5 to 26 carbon atoms such as N-methyl-1,4-diaminocyclohexane, N,N'-dimethyl-1,4-diaminomethylcyclohexane, piperazine, 1,4-diazacycloheptane, 1,15-diazacyclooctacosane and the like; aromatic secondary and mixed primary-secondary diamines having 7 to 21 carbon atoms such as N-methyl-m-phenylenediamine, N,N'-dimethyl-m-phenylenediamine, N-ethyl-m-phenylenediamine, N,N'-diethyl-m-phenylenediamine, N-methyl-p-phenylenediamine, N,N'-dimethyl-p-phenylenediamine, N,N'-diethyl-p-phenylenediamine, N-ethyl-p-phenylenediamine, N-propyl-p-phenylenediamine, N,N'-dimethyl-4-methylphenylenediamine-(1,3), N,N'-dimethyl-2-methylphenylenediamine-(1,3), N,N'-dimethyl-4,4'-diaminodiphenylmethane and the like. Further, polyamines in which the total numbers of primary and secondary amino groups are 2 and the other amino groups are tertiary, such as 1-(2'-aminoethyl)piperazine, 1,4-di(2'-aminoethyl)piperazine can also be employed.

Examples of M are alkali metals such as lithium, sodium, potassium and the like; alkali earth metals such as magnesium, calcium, strontium, barium and the like; and tertiary amines such as trimethylamine, dimethylethylamine, triethylamine, dimethylpropylamine, dimethylisopropylamine, methylethylpropylamine, methyldipropylamine, methylpropylbutylamine, pyridine, N-methylmorpholine, N,N-dimethylaniline, triethylenediamine and the like. However, M is not limited to these examples. Generally, M is a basic substance which can form a sulfonate salt and whose corresponding cation M⁺ does not react with isocyanato radical.

While X and X' are hydrogen atoms or

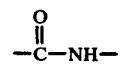

radicals representing amide bonds, the molar ratio of the

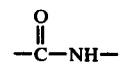

radical should preferably accounts for 30% or less down to zero of the total molar amounts of X and X', because too many biuret bonds, as compared with hydrogen bonds, may cause intermolecular cross-linking that will lead to gelation and the like, thereby reducing the utility value of the product, e.g., the corresponding polymer tends to become thermosetting.

The sulfonate urea compound of the invention may be prepared by reaction of aminoaminocarboxylate expressed by the formula:

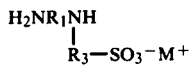 (formula I)

with diisocyanate generally expressed by the formula:

OCNR$_2$NCO (formula II), optionally in the presence of diamine represented by the formula:

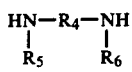 (formula III)

and/or water. If aminoaminocarboxylate (formula I) and diisocyanate (formula II) alone are allowed to react, there will be obtained a compound as given by formula A mentioned above. Meanwhile, if such reaction is accompanied by the addition of diamine (formula III) or water, then there will be obtained a compound as given by formula B or C mentioned above, respectively. As a matter of course, if the reaction is conducted with addition of both diamine and water, there will be produced a compound as given by formula D mentioned above.

The starting material, aminoaminosulfonic acid, or its salt (formula I) is known and may be obtained, for example, by the reaction of propanesultone or butanesultone with diamine as shown in German Pat. No. 120031. Examples of aminoaminosulfonic acid are aliphatic aminoaminopropanesulfonic acids having 5 to 20 carbon atoms such as N-(2-aminoethyl)γ-amino-n-propanesulfonic acid, N-(3-amino-n-propyl)γ-amino-n-propanesulfonic acid, N-(4-amino-n-butyl)γ-amino-n-propanesulfonic acid, N-(6-amino-n-hexyl)γ-amino-n-propanesulfonic acid, N-(8-amino-n-octyl)γ-amino-n-propanesulfonic acid, N-(17-amino-n-heptadicyl)γ-amino-n-propanesulfonic acid; alicyclic- or aliphatic-substituted alicyclic aminoaminopropanesulfonic acids having 9 to 18 carbon atoms such as N-(3-aminocyclohexyl)γ-amino-n-propanesulfonic acid, N-(4-aminocyclohexyl)γ-amino-n-propanesulfonic acid, N-[4-(4-aminocyclohexylmethyl)cyclohexyl]γ-amino-n-propanesulfonic acid; and aromatic or aliphatic- and/or aliphatic-substituted aromatic aminoaminopropanesulfonic acids having 9 to 18 carbon atoms such as N-(m-aminophenyl)γ-amino-n-propanesulfonic acid, N-(p-aminophenyl)γ-amino-n-propanesulfonic acid, N-(p-aminoxylylene)γ-amino-n-propanesulfonic acid, N-[4-(4-aminophenylmethyl)phenyl]γ-amino-n-propanesulfonic acid.

Examples of aminoaminobutanesulfonic acid are aliphatic aminoaminobutanesulfonic acids having C$_6$–C$_{21}$, such as N-(2-aminoethyl)δ-amino-n-butanesulfonic acid, N-(3-amino-n-propyl)δ-amino-n-butanesulfonic acid, N-(4-amino-n-butyl)δ-amino-n-butanesulfonic acid, N-(6-amino-n-hexyl)δ-amino-n-butanesulfonic acid, N-(8-amino-n-octyl)δ-amino-n-butanesulfonic acid, N-(17-amino-n-heptadecyl)δ-amino-n-butanesulfonic acid; alicyclic and aliphatic-substituted alicyclic aminoaminobutanesulfonic acids having C$_{10}$–C$_{19}$, such as N-(3-aminocyclohexyl)δ-amino-n-butanesulfonic acid, N-(4-aminocyclohexyl)δ-amino-n-butanesulfonic acid, N-[4-(4-aminocyclohexylmethyl)cyclohexyl]δ-amino-n-butanesulfonic acid; and aromatic or aliphatic- and/or aliphatic-substituted aromatic aminoaminobutanesulfonic acid having C$_{10}$–C$_{19}$, such as N-(m-aminophenyl)δ-amino-n-butanesulfonic acid, N-(p-aminophenyl)δ-amino-n-butanesulfonic acid, N-(p-aminoxylylene)δ-amino-n-butanesulfonic acid and N-[4-(4-aminophenylmethyl)phenyl]δ-amino-n-butanesulfonic acid.

These aminoaminosulfonic acids may be presented in the form of aminoaminosulfonates neutralized with a prescribed base M and isolated prior to the preparation of the sulfonate urea compound, or as another method aminoaminosulfonic acid may be neutralized with base M and presented without isolation for polymerization to give the sulfonate urea compound.

Typical examples of diisocyanates (formula II) and diamines (formula III) are as previously described.

While the sulfonate urea compound of the invention may be obtained by interfacial polymerization, solution polymerization, and solvent-free polymerization as hereinafter described in detail, aminoaminosulfonate, diamine, or water may, if necessary, be previously mixed before reaction since they do not react with one another in any case.

In the reaction of primary or secondary amino radical with isocyanato radical, whose reaction rates are considerably high, polymerization catalysts are not necessarily required. When accelerating the polymerization rate or using weakly basic aromatic diamines, however, catalysts should preferably be employed. Such catalysts are well known in the art as used in the production of polyurethanes and polyureas, and include tertiary amines such as triethylamine, N-methylmorpholine, N,N,N',N'-tetramethylpropyldiamine, N,N,N',N'-tetramethyl-1,3-butanediamine, N,N,N',N'-tetramethylhexamethylenediamine, N,N-dimethylbenzylamine, N,N-dimethyllaurylamine, N,N-dimethylpiperazine, triethylenediamine and the like; tin compounds such as tributyl tin acetate, dibutyl tin diacetate, dibutyl tin dilaurate, dibutyl tin sulfide, dibutyl tin dichloride, stannic chloride, stannous octoate, stannous oleate and the like; lead compounds such as lead benzoate, lead oleate and the like; cobalt compounds such as cobalt-2-ethylhexoate, cobalt naphthenate, cobalt benzoate and the like; zinc compounds such as zinc naphthenate-2-ethylhexoate and the like; carboxylic acids such as n-butyric acid, valerianic acid and the like; and ureas such as N-phenyl-N'-o-tolylurea. Excluded however, are those which react with amines to produce substances that may destroy sulfonate structure, or to deactivate their own catalytic actions; such as chlorocarboxylic acid, hydrogen chloride, sulfuric acid, etc.

While the sulfonate urea compounds of the invention, as already described, include also those with branched or cross-linked structure resulting from the production of partial biuret bonds due to the reaction of N-hydrogen radical of urea bond with isocyanato radical, formation of such branched or cross-linked structure may be facilitated by such catalysts as dibutyl tin diacetate, tributyl tin acetate, and triethylenediamine, that accelerate the ureaisocyanate reaction. Accordingly, if such branched or cross-linked structure is not desired, these catalysts are not used. As for the catalysts to favor the formation of biuret bonds, tin compounds, such as dibutyl tin diacetate and tributyl tin acetate; triethylenediamine; and aforesaid zinc compounds are preferred.

Many of the aminoaminosulfonates as given by formula I and their corresponding aminoaminosulfonic acids have high melting points, and dissolve in highly-polar protic solvents, such as water and low carbon alcohols, as well as in high-polar solvents with high dielectric constants, such as N,N-dimethylformamide and dimethylsulfoxide, though they are hardly soluble in other lowly-polar solvents. However, aminoaminosulfonic acid with lower ionic density, that is, with higher molecular weight has a lower melting point and higher solubility. Therefore, the polymerization method and conditions should be selected in accordance with the melting point and solubility of the aminoaminosulfonic acid or its salt (formula I).

When using protonic solvents such as water, etc., polymerization can be conducted if the reactivity of aminoaminosulfonate (formula I) is sufficiently higher than that of the protic solvents or if there is used any of those catalysts which preferentially accelerate the reaction with amino radicals, such as divalent tin carboxylates e.g. stannous octoate, stannous laurate or N-ethyl morpholine. Also, polymerization can be achieved in case there is applied the so-called interfacial polymerization method in which diisocyanate (formula II) is dissolved in a nonpolar solvent immiscible with the protic solvents, aminoaminosulfonate (formula I) is dissolved in a protic solvent, and the resulting two solutions are mixed with each other, and then polymerization takes place at the interface.

Most widely used are polar aprotic solvents such as dimethylformamide and dimethylsulfoxide. A solution of aminoaminosulfonate (formula I) for the polymerization with diisocyanate (formula II) may be prepared by dissolving aminoaminosulfonic acid and a base M in these solvents, or as another method by dissolving aminoaminosulfonate (formula I) directly in these solvents. In the preparation of the solution of the aminoaminosulfonate according to the former case, however, if hydroxides of alkali metals or alkali earth metals, are used as a base M, they give, by neutralization, water or other low molecular-weight substances, and the low molecular weight substances may react with the isocyanato radical to interfere with the polymerization. Further the released water may react with isocyanato to give rise to decarboxylation and the formation of urea bonds. The latter case has no such weak points but has other disadvantages as such: increase of steps of a process due to the additional previous preparation of aminoaminosulfonate (formula I) and poorer solubility of aminoaminosulfonate (formula I) as compared with the former case. Further, polymer electrolyte of this invention is generally utiized in the form of an aqueous solution, which can be directly prepared by the aforesaid aqueous interfacial polymerization method. According to the solution polymerization method, however, the aqueous solution can be obtained only by dissolving in water polymer electrolyte which has been isolated by precipitation in a non-solvent. Meanwhile, if the object is to obtain a formed product of the polymer electrolyte by the dry or wet process, solution polymerization method is advantageous in that the formed product may easily be obtained by the evaporation of the solvent of the polar aprotic solvent or by extruding polymer electrolyte solution into a non-solvent.

Solvent-free polymerization may be achieved if the melting point of aminoaminosulfonate (formula I) is low or its amine value is small, that is, for example, if $R_1$ in formula I contains any ether bond or if $R_1$ is selected from any of a considerably long aliphatic hydrocarbon radical having a low melting point, or polyether or polyester radicals. Meanwhile, with a large amine value, the solvent-free polymerization can be conducted by admixing a filler which does not react with either isocyanato or amino radicals. The filler is herein meant by a substance which is, unlike the aforesaid solvent, not necessarily required to dissolve the aminoaminosulfonate (formula I) and diisocyanate (formula II) and can produce a polymer mixture containing it to exhibit satisfactory properties as a high molecular composite. Typical examples of such diluting filler which would not react with diamine and diisocyanate include inorganic materials such as calcium carbonate, glass fiber, ceramic wool, rock wool, fine gravel, perlite, silica, alumina, silica balloon, glass balloon, barium sulfate, etc.; organic materials such as wood, pulp, natural or synthetic fibers, waste paper, fragments of plastics, etc.; and metal powder such as iron powder, copper powder, aluminum powder, etc.

Even with a large amine value, foaming products may be produced by high-rate exothermic reaction if the melting point of aminoaminosulfonate (formula I) is low. The solvent-free polymerization may be conducted by mixing aminoaminosulfonate (formula I) with diisocyanate (formula II) in the presence or absence of any fillers as occasion demands, polymerizing them at a proper temperature for a suitable period of time, and preferably curing the product at a higher temperature for further completing the polymerization. Although such solvent-free polymerization is advantageous in that a formed product can be produced in one step, it has a defect that it is difficult to prepare thermoplastic or soluble polymers.

While the polymerization temperatures for the aforementioned polymerization in protic solvent (e.g., aqueous interfacial polymerization), polar aprotic solution polymerization, and solvent-free polymerization may vary with the situations, it is desired that a relatively low temperature should be used at the initial stage in any of these cases. This is because the initial molecular weight of the polymer is desired to be sufficiently increased for obtaining satisfactory properties of a high molecular-weight substance by giving priority so much as possible to the production of urea bonds resulting from the reaction of aminoaminosulfonate (formula I), as well as diamine (formula III) used at need, with diisocyanate (formula II). In preparing foamed products by high-rate polymerization, however, foaming is preformed by taking advantage of the production of heat due to the rapid deposition of polymerization heat, regardless of initial temperature, so that cross-linking reaction may be caused as a side reaction, usually rendering the so-called initial or primary molecular weight not very high, though it is sufficient for the properties of a foamed product. As the polymerization temperature increases, the significant differences between the reactions of the amino radical, water, and urea bond on the isocyanato radical are reduced, hardly increasing the primary molecular weight, and generations of cross linkage, decarboxylation and urea bond may often increase. Addition of a catalyst may cause the significant difference in the selective reactivity of the active protons, such as amino radicals, urea radicals, and water, with the isocyanato radical reduced, depending on the kind of catalyst. Therefore, it is desired that the noncatalytic reaction should be employed for the earlier stages of polymerization, and the catalyst should be added after the reaction between the amino and isocyanato radicals has been fully carried out. The reason is that the non-catalytic reaction may often take advantage of the normal relation amino radical $>$ water $\geqq$ urea as regards the reactivity with the isocyanato radicals. The reaction of a small amount of remaining isocyanato radicals can be completed by raising the polymerization temperature at the end of the polymerization, that is, at the time when most of the isocyanato radicals have finished reaction. In this case, the aforesaid competing reaction, if any, will hardly have a bad influence on the properties of the polymer, but, on the contrary, increase the molecular weight and eliminate the harmful effects attributable to the remaining isocyanato radicals. In general, polymerization with protic solvents should preferably be conducted at a low temperature; the aprotic solution polymerization may of course be performed at a relatively high temperature, and the solvent-free polymerization may be carried out in ranges of both high and low temperatures.

While the common features and advantages of the preparing method of this invention have been described above, there will now be described in detail the interfacial polymerization, solution polymerization, and solvent-free polymerization methods.

INTERFACIAL POLYMERIZATION

The solvents to be essentially employed in the interfacial polymerization method are water and organic solvents insoluble in water. The latter may be any organic solvents that dissolve diisocyanate (formula II) and do not or react very slowly with isocyanato radical, including aliphatic hydrocarbons, or halides or sulfides thereof, such as cyclohexane, chloroform, methylene chloride, carbon tetrachloride, 1,2-dichloroethane, tetrachloroethylene, carbon disulfide, etc.; and aromatic hydrocarbons, or halides or nitro derivative thereof, such as benzene, xylene, chlorobenzene, dichlorobenzene, nitrobenzene, etc., though these are given only by way of examples. Strictly speaking, this interfacial polymerization should be called interfacial polyaddition reaction, which is different from the so-called interfacial polycondensation reaction in which the conventional Schotten-Baumann reaction is utilized. One of the greatest differences between these two reactions is that in the interfacial polycondensation reaction alkali is added to the aqueous system for neutralization in order to remove hydrogen chloride or other low molecular-weight by-products and direct the equilibrium of reaction toward the polymer production. Typical examples of such addition of alkali are conducted in preparation of polyamide by the interfacial polycondensation reaction of dibasic acid chloride and diamine, preparation of polyurethane by the interfacial polycondensation reaction of dichloroformic ester and diamine, or preparation of polyphenyl ester by the interfacial polycondensation reaction of dibasic acid chloride and bisphenol, for example. The interfacial polycondensation reaction is an equilibrium reaction in which polymerization does not proceed unless the low molecular-weight by-products are removed, while in the interfacial polyaddition reaction, which is not such an equilibrium reaction, alkali is not required to be added because no low molecular-weight products are formed. The reaction of interfacial polyaddition reaction takes place, like the interfacial polycondensation reaction, in organic solvent layers, so that decarboxylation due to a reaction between isocyanato and water and resulting formation of urea bonds may be desirably avoided. In this respect, the interfacial polyaddition reaction is fundamentally different from the aqueous polymerization disclosed, for example, in German Pat. No. 1282962. In polymerization, the aminoaminosulfonate (formula I) and diamine (formula III) (if required) are dissolved in water, while the diisocyanate (formula II) is dissolved in the aforesaid organic solvent that does not dissolve in water. The aqueous solution of aminoaminosulfonate (formula I) may be prepared also by dissolving the aminoaminosulfonic acid and base M in water for neutralization instead of directly dissolving the aminoaminosulfonate (formula I) in water.

Concentrations of the reactants in the solvents may be selected rather voluntarily, taking their upper limits as such that the agitation of the produced polymer solution or emulsion is nearly impossible. However, higher viscosity may retard the polymerization or cause uneven polymerization, so that the proper concentration may range from 0.1% to 40%, preferably from 1% to 30%.

Although the upper limit of the polymerization temperature is 100° C. because of the aqueous system being used, actual polymerization is performed below the boiling point of an organic solvent used in the reaction if it boils below 100° C. Meanwhile, if the temperature increases as stated above, it leads to increases of decarboxylation owing to the reaction of the water with diisocyanate (formula II) and resulting generation of urea bond, and it accompanies the occurrence of hydrolysis. Therefore, it is advisable to perform the polymerization usually at about 60° C. or below. Although the minimum limit of the polymerization temperature should only be higher than the freezing temperature of the aqueous solution, it frequently drops below 0° C. owing to the freezing point depression attributable to the existence of the aminoaminosulfonate (formula I) and diamine (formula III). However, if the freezing point of the organic solvent is higher than 0° C., as is the case with, for example, benzene, and the concentration of the solution is too low to cause freezing point depression down to 0° C., then the polymerization is performed at a temperature higher than 0° C. After all, the main polymerization reaction is performed preferably at a temperature ranging from the freezing point of the polymerization system to 60° C., most preferably from 0° C. to 35° C.

While the objective sulfonate anion polyurea with satisfactory high molecular property may be obtained by the main polymerization reaction in which reaction of most of the isocyanato radicals present is completed, it is desired that curing should finally be performed at a somewhat elevated polymerization temperature in order to complete the reaction of the small amount of remaining isocyanato radicals as aforesaid. In doing this, heating is usually performed at a temperature 5° to 30° C. higher than the main polymerization temperature. Further, as previously described, polymerization may be accelerated by the addition of such catalysts as stannic dicarboxylate and N-ethylmorpholine that selectively accelerate the reaction of amino radicals with isocyanato radicals and hardly have any effects on the reaction between isocyanato radicals and water. Although such catalysts may be added at the initial stage of the main polymerization reaction, it is most advisable to add them at the end of the main polymerization, that is, at a point of time when most of the isocyanato radicals have finished reaction and then to continue polymerizing at the same temperature in order preferably to avoid the side reactions as already mentioned.

Thus obtained reaction product may be isolated or purified by the following process, for example. Since hardly any sulfonate polyurea exists in the organic solvent phase because of its high-polarity, the aqueous solution phase containing the product may be obtained by separating and removing the organic solvent phase by decantation or by means of a separating funnel when aqueous and organic-solvent phases are separated in layers from each other. While the aqueous solution of the sulfonate polyurea may be cleared of some remaining organic solvent by evaporation, and used directly as a product, a sulfonate polyurea may, if necessary, be also isolated by the precipitation method as mentioned later. If there exists any water-insoluble polymer, it should only be previously isolated by filtration. If the reaction mixture is in the form of emulsion, suspension, paste, or cream, prohibiting the aforesaid layer separation, the organic solvent is removed by vacuum evaporation, and then the aforementioned treatment is performed. If there can be obtained no uniform phase for all that, the sulfonate polyurea can be isolated by evaporating out a proper amount of water as well as the organic solvent to concentrate the reaction mixture and then adding the resulting concentrate to a solvent that is soluble in water but does not dissolve sulfonate polyurea for precipitation. Since the isolated substance may contain both water-soluble and water-insoluble components, an aqueous solution composed of the water-soluble component alone may be obtained by again dissolving both these components in water and filtering out the insoluble portion in order to separate these components from each other. While the obtained solution may be offered directly as a final product as aforesaid, water-soluble sulfonate polyurea can be isolated by precipitation, if required. The precipitation solvent may be selected from nitriles such as acetonitrile and propionitrile; ketones such as acetone and methyl ethyl ketone. The precipitation solvent, however, is not limited to the aforesaid substances, but may be found among solvents that have permanent dipoles hardly capable of free rotation and can never or hardly dissolve the sulfonate polyurea. Non-polar solvents or polar solvents having free-rotatable chemical bonds tends to produce oily substances.

SOLUTION POLYMERIZATION

Polar aprotic solvents are preferred in the solution polymerization because the electrolyte, that is, sulfonate polyurea may hardly be dissolved in solvents with low-polarity and also because aprotic solvents with no active hydrogens are required to minimize the reaction between the isocyanato radicals and solvent. Such solvents include tertiary amides such as N,N-dimethylformamide, N,N-dimethylacetamide, and N-methylpyrrolidone; aprotic organic sulfur oxides such as dimethylsulfoxide; and triesters of phosphoric acid such as triethyl phosphate and tri-n-butylphosphate. Aminoaminosulfonate (formula I) with low density of electric charge or some lithium salt may be dissolved even with a solvent having a lower polarity than those of the above-mentioned polar solvents. On the other hand, when the polarity of the aminoaminosulfonate (formula I) is relatively high, it may hardly be dissolved even with the above-mentioned polar solvents. In such a case the solubility may be improved by adding some electrolytes that do not react with diisocyanate (formula II) but dissolve in the polar solvents. Such electrolyte may be selected from salts such as fluorides, chlorides, perchlorates and nitrates of alkaline metals including lithium, sodium, and potassium; zinc chloride; mercury chloride; alkaline metal alcoholates such as lithium methylate, sodium methylate, and potassium ethylate; salts such as halide, perchlorate, tetrafluoroborate, nitrate, acetate and sulfonate of tetraalkylammonium; tetrarylborates such as tegraphenylborate, for example.

While in polymerization the aminoaminosulfonate (formula I) is dissolved in the aforesaid polar solvent, any aforesaid electrolyte may be added as the solubilizing agent, if necessary. In doing this, the electrolyte solubilizing agent is added at a level below its saturation solubility in the polar solvent, though a little amount of solubilizing agent to add may be enough because such solubility is usually low. Diamine (formula III) may be added if required to the solution of aminoaminosulfonate (formula I). The proper solution of aminoaminosulfonate (formula I) may also be prepared by dissolving the aminoaminosulfonic acid and base M in the polar solvent for neutralization instead of directly dissolving the aminoaminosulfonate (formula I) in the polar solvent. In this case, however, water may sometimes be performed by the neutralization as aforesaid. The water may be removed by addition of any conventional dehydrating agent that do not react with the aminoaminosulfonate (formula I), diisocyanate (formula II), diamine (formula III) and sulfonate polyurea. Such dehydrating agent may be selected from sodium sulfate, magnesium sulfate, calcium sulfate, copper sulfate, aluminum sulfate, alumina, and silica gel, for example. Although the diisocyanate (formula II) may be added directly to the solution, it may cause a rapid exothermic reaction if the concentration is high or the basicity of the amine component is strong. This may be avoided by diluting the diisocyanate (formula II) with the polar solvent and adding it gradually to the solution of amine component.

Although the polymerization may be performed in the air, it should preferably be done in an inert-gas atmosphere of dehumidified atmosphere in order to minimize the denaturing of diisocyanate, aminoaminosulfonate (formula I) and/or diamine (formula III) by carbon dixoxide and water in the air.

Although the polymerization temperature may be at any level higher than the freezing point and lower than the boiling point of the polymerization system, higher temperature is liable to cause production of the aforementioned biuret bonds due to the reaction between the urea bonds and isocyanato radicals as well as accompanying side reactions such as cross-linking reaction. Therefore, the polymerization should be conducted usually at a temperature below 200° C., preferably above the freezing point and up to 100° C. Practically, in order to minimize the side reactions, the first stage polymerization is performed at a relatively low temperature, e.g., the normal temperature (20° C.), and the second stage polymerication is started after most of the isocyanato radicals have reacted. In the second stage polymerization, the reaction temperature may be substantially the same as that of the first stage, though the polymerization reaction is further completed by the addition of a catalyst for accelerating the reaction between the aforesaid isocyanato and amino radicals. If the second stage polymerization cannot yet provide a high molecular-weight polymer, leaving a small amount of isocyanato radicals, it is advisable to perform third stage polymerization at a temperature 5° to 100° C. higher than those of the first and second stages. Not all these three stages of polymerization are required; the first stage alone may often be enough when the polymerization rate is high, or aromatic diisocyanate and aliphatic diamine reactants react with each other, or if high concentration of the reactants is used for the reaction. The first stage of polymerization may be directly followed by the third stage, or otherwise the second stage reaction may be firstly performed in the case with very low polymerization rate. In a reaction system with high polymerization rate, however, it is not desired from a point of view of side reactions to start the second or third stage of polymerization neglecting the first stage polymerization.

If the polymerization is performed under the above-mentioned conditions, it will be completed within a period of time ranging from a few minutes to approximately 10 hours. Although the reactant concentration may be at any level that allows the reaction system to be stirred or kneaded, low concentration will retard the polymerization or reduce the yield. On the other hand, too high concentration may accelerate the polymerization, but will cause cross-linking reaction or other side reactions as well as provide uneven polymer composition. Accordingly, the polymerization should usually be performed with a reactant concentration of 1% to 50%, moast preferably 5% to 30%.

While a solution of thus obtained sulfonate polyurea may be used as it is depending on the application, the polymer itself may be isolated by precipitation with the aforesaid precipitation solvent. Further, films may be manufactured by evaporating the solution (dry process), while films or fibers may be manufactured by discharging the solution into a non-solvent (wet process).

SOLVENT-FREE POLYMERIZATION

The solvent-free polymerization method may be applied to the case in which the aminoaminosulfonate (formula I) has a low melting point or its amine value is small, or a mixture of the aminoaminosulfonate and diamine (formula III) has a low melting point or small amine value, as well as to mixtures containing the aforementioned fillers. In the latter case, the polymerization is generally performed immediately after mixing the materials and pouring or filling the mixture into any suitable container or casting mold. Though catalysts are hardly required because the polymerization rate is usually high, they should suitably be used when using any fillers for dilution. The polymerization is performed usually around the normal temperature, though cooling or heating may be effected as occasion demands. After the polymerization has nearly completed, the reaction system should preferably be heated at a temperature higher than the polymerization temperature at the first stage for a suitable period of time in order further to stabilize the properties of the polymer. The preferred temperature for the first stage of polymerization is usually 0° C. to 100° C., while the so-called curing temperature in the second stage ranges from 50° C. to 200° C. The polymerization time varies with the polymerization temperature, filling material, and the reactant; 30 minutes to 30 hours for the first stage of polymerization, and 0 to 30 hours for the curing reaction of the second stage.

The sulfonate polyurea of this invention as a high molecular electrolyte has the following distinguished properties.

(a) Water-solubility or hydrophile property.
(b) Flocculations.
(c) Surface activity.
(d) Moisture- and water-absorptive properties.
(e) Antistatic property.
(f) Ionizability.
(g) Ability to chelate with metals.
(h) Ion-exchangeability.
(i) Buffer action.
(j) High dielectric property.
(k) Safety to organisms.

All these properties except the one given by (k) are entirely attributable to the characteristic effects owing to the existence of x-component; some properties are found more definitely with higher rate of x-component, and others indicate optional improvement of the conventional polyureas or other components caused by the addition of x-component.

Taking advantage of the above properties the polyurea of this invention may be used for a wide variety of applications including antistatic agents, dye fixing agent, flocculants, sensitizers, photosensitive agents, auxiliaries for ink or paints, surface-active agent, ion-exchange resins, adsorbents, chelating agents, electrodeposition paints, water-soluble adhesives, reactive paints, no-pollution agricultural chemicals, cosmetic materials, dielectrics, oxidants and reductants, pH controllers, soil conditions, etc.

This invention will be more fully understood from the following Examples. In these Examples diamines with radical $R_1$ are selected only from aliphatic, aliphatic-substituted aromatic, and aromatic diamines, and diisocyanates with radical $R_3$ are selected only from aliphatic, aliphatic-substituted aromatic, and aromatic diamines. Hereupon, according to the invention, it has been found that the reactivity of diamines is subject to a relation: aliphatic>aromatic, while that of diisocyanates is subject to a relation: aromatic>aliphatic, the reactivity of compounds of other groups being intermediate between those of the aromatic and aliphatic.

EXAMPLE 1

50 ml of degassed distilled water, 1.20 g of sodium hydroxide, and 7.15 g of N-(6-amino-n-hexyl)γ-amino-n-propanesulfonic acid (m.p. 161.0° to 163.0° C.) were placed in a four necked pear-shaped separable flask (200 ml capacity) equipped with a dropping funnel leading from a nitrogen inlet, a Liebig condenser leading to a nitrogen outlet, and a stirrer, and were subjected to nitrogen-substitution and stirred while keeping the flask at 24° C. A solution of 6.00 g of hexamethylene diisocyanate in 50 ml of carbon tetrachloride was dropped stepwise into the stirred mixture through dropping funnel for 70 minutes. After completion of such dropping, the mixture was kept under stirring for further 3 hours, added by 0.0160 g of stannous octoate, and then subjected to one more hour's polymerization. While being stirred continuously, the reaction mixture was added to a large excess amount of acetonitrile, and a polymer was isolated (yield 12.1 g, yield rate 84.3%, softening point 103° to 116° C.). This polymer was pulverized and added to 726 ml of distilled water, and soluble and insoluble portions were separated thereof by filtration. The resulting filtrate was concentrated by vacuum evaporating water, and the concentrate was added to a large excess amount of acetonitrile for precipitation, and thus there was obtained a colorless, powdered polymer (yield 10.2 g, yield rate 71.1%, softening point 98° to 102.5° C., $\eta_{inh}{}^{30°\ C.}$/DMSO=0.596). This polymer exhibited asymmetric stretching vibration of sulfonate at 1,180 to 1,170 cm$^{-1}$ of infrared absorption spectrum, symmetric stretching vibration of sulfonate at 1,050 to 1,030 cm$^{-1}$, absorption of amide I at 1,560 to 1,540 cm$^{-1}$, and absorption of amide II. Measurement of the nuclear magnetic resonance spectrum of the polymer by means of d$_6$-dimethyl sulfoxide solvent revealed the formation of a sulfonate polyurea with a structure given by

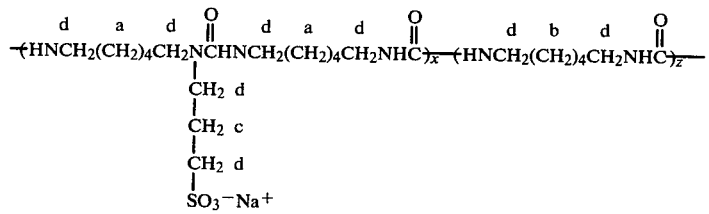

In the above structural formula, the multiplet signals ranging from 0.84 to 1.60δ ppm are assigned to the (a) and (b) radicals, the multiplet signals ranging from 1.70 to 1.90δ ppm are assigned to the (c) radical, the multiplet signals ranging from 2.70 to 3.65δ ppm are assigned to the (d) radical. Since in this Example no diamine are used, component y should be zero. The relation between x and z, as obtained from the integral values of (a)+(b) and (c), is as follows:

$$\frac{a+b}{c} = \frac{8x+4z}{x} = 8.30,$$

$$x + z = 1.$$

Accordingly, x=0.930, so that this polymer was found to be a sulfonate polyurea to fulfil 0.1<100x<100 and D<100z<50 (here x+z=1).

Subsequently, a film was prepared by pouring an aqueous solution of this sulfonate polyurea over a Teflon-coated plate and evaporating water at 50° to 100° C. This film was soluble in water, and exhibited no electrical charge by either friction or peeling. 0.125 g of this polymer was dissolved in 25 ml of m-cresol, and the solution viscosity was measured at 30° C. While the flow time of the solvent was 107.7 seconds, that of this solution was 91.3 seconds, indicating reduction of viscosity. Thus the viscosity of m-cresol reduced because this polymer is an electrolyte stronger enough than m-cresol to restrain m-cresol from ionization.

EXAMPLE 2

Employing the same devices as those of Example 1, 50 ml of degassed distilled water, 1.20 g of sodium hydroxide, and 7.15 g of N-(6-amino-n-hexyl)-γ-amino-n-propanesulfonic acid were placed in the flask, subjected to nitrogen-substitution, and stirred while keeping the flask at 23° C. A solution of 8.80 g of 4,4′-diphenylmethanediisocyanate in 22 ml of carbon tetrachloride was dropped stepwise into the stirred mixture through the dropping funnel for 30 minutes. After completion of such dropping, the mixture was kept under stirring for the further 1 hour and a half, and then the liquid temperature was elevated to 50° C. for additional 30 minutes' agitation. Thereafter, 50 ml of degassed distilled water and 50 ml of carbon tetrachloride were added to the mixture for 2 hours' polymerization at 23° C., and then 0.0200 g of stannous octoate was added for additional 30 minutes' polymerization. While being stirred continuously, the reaction mixture was added to a large excess amount of acetonitrile, and a polymer was isolated (yield 15.3 g, yield rate 89.2%, softening point 230° to 240° C., $\eta_{inh}{}^{30°\ C.}$/DMSO=1.53). This polymer was pulverized and added to 918 ml of distilled water, and soluble and insoluble portions were separated by filtration. The resulting filtrate was concentrated by vacuum evaporating water, and the concentrate was added to a large excess amount of acetonitrile for precipitation, and thus there was obtained a colorless, powdered polymer (I) (yield 7.77 g, yield rate 45.3%, softening point 224° to 228° C., $\eta_{inh}{}^{30°\ C.}$/DMSO=1.25). From the infrared absorption spectrum and nuclear magnetic resonance spectrum, this polymer (I) was found to have a composition given by y=0, x=0.961, 0.1<100x<100, and 0<100z<50 (here x+z=1). A film was prepared by pouring an aqueous solution of this polymer over a Teflon-coated plate and evaporating water at a temperature ranging from 50° to 100° C. This film was soluble in water, and exhibited no electrical charge by either friction or peeling. Further, a flocculant test was conducted for the polymer (I). The subject liquid used was a suspension of barium sulfate of 2,260 ppm concentration. 0.1 or 0.01 wt.% solution of the polymer (I) was added to the suspension contained in a 250 ml plugged messcylinder. The messcylinder was reversed 10 times and then left at rest, and the clear volume was measured relatively to time. As a result, it was found that 0.6 to 1.0 ppm addition of the solution led to the most satisfactory flocculation.

The dielectric properties of the water-soluble polymer (I) were measured on a dielectric loss meter (from Ando Denki Co., Ltd.). The measurement was performed at 20° C. by pressure-molding the powdered polymer under a pressure of 100 kg/cm$^2$. Consequently, there were exhibited such low dielectric constants as show below, despite the polar radical contained.

| Hz | ε′ | tanδ | ε″ |
|---|---|---|---|
| 60 | 2.80 | 0.0965 | 0.270 |
| 1,000 | 2.48 | 0.0550 | 0.136 |
| 10,000 | 2.32 | 0.0438 | 0.102 |

In order to observe the surface active effect of the water-soluble polymer (I), the surface tension was measured with varied concentrations of the polymer in water. There was employed the Denui's Surface & Interfacial Tension Meter (available from Shimazu Seisaku-sho Co., Ltd.) with liquid temperature at 21.0° C. It was found that the surface tension hardly charge with the concentrations, as indicated below.

| Concentration (wt%) | 0 | $5\times10^{-4}$ | $5\times10^{-3}$ | $5\times10^{-2}$ | $5\times10^{-1}$ |
|---|---|---|---|---|---|
| Surface Tension (dyn/cm) | 70.3 | 68.7 | 69.6 | 65.3 | 66.2 |

The water-insoluble portion was a colorless, powdered polymer (II) (yield 7.28 g, yield rate 42.4%, softening point 236° to 248° C., $\eta_{inh}^{30°\ C.}$/DMSO=1.27). From the infrared absorption spectrum and nuclear magnetic resonance spectrum, this polymer (II) was found to be a sulfonate polyurea with a composition given by y=0, x=0.924, 0.1<100x<100, and 0<100z<50 (here x+z=1).

EXAMPLE 3

Employing the same devices as those of Example 1, 100 ml of dimethylformamide, 0.720 g of lithium hydroxide, 7.15 g of N-(6-amino-n-hexyl)γ-amino-n-propanesulfonic acid, 2.50 g of lithium chloride, and 0.063 g of dibutyltindilaurate were placed in the flask, subjected to nitrogen-substitution, and stirred while keeping the flask at 22° C. 6.00 g of hexamethylenediisocyanate was dropped stepwise into the stirred mixture through the dropping funnel for 15 minutes. After completion of such dropping, the mixture was kept under stirring for the further 2 hours, and then the liquid temperature was elevated to 80° C. for 1.5 hours' polymerization. While being stirred continuously, the reaction mixture was added to a large excess amount of acetonitrile, and a polymer was isolated. This polymer was pulverized and added to 34 ml of distilled water, and soluble and insoluble portions were separated thereof by filtration. The water-insoluble portion was a colorless, powdered polymer (I) (yield 10.6 g, yield rate 64.8%, softening point 196° to 198° C., $\eta_{inh}^{+°\ C.}$/DMSO=1.13). From the infrared absorption spectrum and nuclear magnetic resonance spectrum, this polymer (I) was found to be a sulfonate polyurea with a composition given by y=0, z=0 and x=1. Further, 0.127 g of this polymer (I) was dissolved in 25 ml of m-cresol, and the solution viscosity was measured at 30° C. While the flow time of the solvent was 107.7 seconds, that of this solution was 108.6 seconds, indicating hardly any increase in viscosity. The viscosity of m-cresol increased by such a small degree because this polymer is an electrolyte stronger enough than m-cresol to restrain m-cresol from ionization. The filtrate was concentrated by vacuum evaporating water, and the concentrate was added to a large excess amount of acetonitrile for precipitation, and thus there was obtained a transparent, gummy polymer (II) (yield 2.63 g, yield rate 16.1%, $\eta_{inh}^{30°\ C.}$/DMSO=0.142, $\eta_{inh}^{30°\ C.}$/H2O=0.0378). From the infrared absorption spectrum and nuclear magnetic resonance spectrum, this polymer (II) was found to be a sulfonate polyurea with a composition given by y=0, z=0 and x=1.

EXAMPLE 4

Employing the same devices as those of Example 1, 100 ml of dimethylformamide, 0.720 g of lithium hydroxide, 7.15 g of N-(6-amino-n-hexyl)γ-amino-n-propanesulfonic acid, 2.50 g of lithium chloride, and 0.131 g of dibutyltindilaurate were placed in the flask, subjected to nitrogen-substitution, and stirred while keeping the flask at 80° C. A solution of 8.80 g of 4,4'-diphenylmethanediisocyanate in 12 ml of dimethylformamide was dropped stepwise into the stirred mixture through the dropping funnel for 35 minutes. After completion of such dropping, the mixture was subjected to 2 hours' polymerization as it was. While being stirred continuously, the reaction mixture was added to a large excess amount of acetonitrile, and a polymer was isolated. This polymer was pulverized and added to 496 ml of distilled water, and soluble and insoluble portions were separated thereof by filtration. The resulting filtrate was concentrated by vacuum evaporating water, and the concentrate was added to a large excess amount of acetonitrile for precipitation, and thus there was obtained a colorless, powdered polymer (I) (yield 5.56 g, yield rate 29.0%, softening point 111° to 116° C., $\eta_{inh}^{30°\ C.}$/DMSO=0.458). From the infrared absorption spectrum and nuclear magnetic resonance spectrum, this polymer (I) was found to be a sulfonate polyurea with a composition given by y=0, z=0 and x=1. A film was prepared by pouring an aqueous solution of this polymer over a Teflon-coated plate and evaporating water at a temperature ranging from 50° to 100° C. This film was soluble in water, and exhibited no electrical charge by either friction or peeling. The water-insoluble portion was a pale-yellow, powdered polymer (II) (yield 11.9 g, yield rate 62.1%, softening point 222° to 226° C., $\eta_{inh}^{30°\ C.}$/DMSO=1.08). From the infrared absorption spectrum and nuclear magnetic resonance spectrum, this polymer (II) was found to be a sulfonate polyurea with a composition given by y=0, z=0 and x=1. Further, 0.128 g of this polymer (II) was dissolved in 25 ml of m-cresol, and the solution viscosity was measured at 30° C. While the flow time of the solvent was 107.7 seconds, that of this solution was 90.1 seconds, indicating substantial reduction of viscosity. Thus the viscosity of m-cresol reduced because this polymer is an electrolyte stronger enough than m-cresol to restrain m-cresol from ionization.

EXAMPLE 5

Employing the same devices as those of Example 1, 50 ml of degassed distilled water, 1.20 g of sodium hydroxide, 6.90 g of N-(p-aminophenyl)γ-amino-n-propanesulfonic acid (m.p. 282.0° to 285.0° C.), and 0.146 g of stannous octoate were placed in the flask, subjected to nitrogen-substitution, and stirred while keeping the flask at 18° C. A solution of 6.00 g of hexamethylenediisocyanate in 50 ml of carbon tetrachloride was dropped stepwise into the stirred mixture through the dropping funnel for 40 minutes. After completion of such dropping, the mixture was kept under stirring for the further 3 hours as it was, and then the liquid temperature was elevated to 45° C. for 6 hours' polymerization. While being stirred continuously, the reaction mixture was added to a large excess amount of acetonitrile, and a brown, powdered polymer was isolated (yield 14.0 g, yield rate 99.3%, softening point 119° to 121° C., $\eta_{inh}^{30°\ C.}$/DMSO=0.568). This polymer was pulverized and added to 280 ml of distilled water, which was dissolved and filtered. There was produced no water-insoluble matter. The resulting filtrate was concentrated by vacuum evaporating water, and the concentrate was added to a large excess amount of acetonitrile for precipitation, and thus there was obtained a pale-brown, powdered polymer (yield 12.3 g, yield rate 87.2%, softening point 126.5 to 128.0° C., $\eta_{inh}^{30°\ C.}$/DMSO=0.577). From the infrared absorption spectrum and nuclear magnetic resonance spectrum, this polymer was found to be a sulfonate polyurea with a composition given by y=0, z=0 and x=1. A film was prepared by pouring an aqueous solution of this polymer over a Teflon-coated plate and evaporating water at a temperature ranging from 50° to 100° C. This film was soluble in water, and exhibited no electrical charge by either friction or peeling.

EXAMPLE 6

Employing the same devices as those of Example 1, 90 ml of dimethylformamide, 0.720 g of lithium hydroxide, 6.90 g of N-(p-aminophenyl)γ-amino-n-propanesulfonic acid, 2.50 g of lithium chloride, and 0.118 g of dibutyltindilaurate were placed in the flask, subjected to nitrogen-substitution, and stirred while keeping the flask at 18° C. A solution of 7.51 g of 4,4'-diphenylmethanediisocyanate in 10 ml of dimethylformamide was dropped stepwise into the stirred mixture through the dropping funnel for 20 minutes. After completion of such dropping, the temperature was elevated to 40° C. for 3.5 hours' polymerization. While being stirred continuously, the reaction mixture was added to a large excess amount of acetonitrile, and a polymer was isolated. This polymer was pulverized and added to 382 ml of distilled water, which was dissolved and filtered. There was produced no water-insoluble matter. The resulting filtrate was concentrated by vacuum evaporating water, and the concentrate was added to a large excess amount of acetonitrile for precipitation, and thus there was obtained a gray, powdered polymer (yield 13.2 g, yield rate 76.3%, softening point 220° to 228° C.). From the infrared absorption spectrum and nuclear magnetic resonance spectrum, this polymer was found to be a sulfonate polyurea with a composition given by y=0, z=0 and x=1. A flocculant test was conducted for this polymer. The subject liquid used was a suspension of barium sulfate of 2,260 ppm concentration. 0.1 or 0.01 wt.% aqueous solution of the polymer was added to the suspension contained in a 250 ml tapped messcylinder. The messcylinder was reversed 10 times and then placed in state, and the volume of clear portion was measured relatively to time. As a result, 1.0 ppm addition of the solution has given a satisfactory agglomeration, and it is confirmed that the polymer exhibits chelate effect with a metal and ion-exchange effect.

EXAMPLE 7

25.2 g of N-(6-amino-n-hexyl)δ-amino-n-butanesulfonic acid lithium salt, 320 g of ω,ω'-di-(aminotolylcarbamoyl)polytetramethylene glycol (amine value 35.1), 19.8 g of 4,4'-diphenylmethanediamine, 6.01 g of ethylenediamine, and 559 g of silica powder were placed in a 5 l beaker, heated to 80° to 100° C. for fusing them, and then cooled to 60° C. Thereafter, 69.6 g of tolylenediisocyanate (2,4-tolylenediisocyanate:2,6-tolylenediisocyanate=80:20) was added to the cooled mixture and again fully mixed. Subsequently, the mixture was cast in two parallel Teflon-coated iron plates, and heated at the room temperature for 1 hour, then at 80° C. for 3 hours, and finally at 120° C. for additional 1 hour, and then restored to the room temperature, and a plastic plate was removed from the mold. This sample was subjected to 5 seconds' application of 15KV voltage at a distance of 5 cm for electrification at a level of 3 to 4×10⁻⁹ C/cm², left in an atmosphere at 20° C. and 40% to 65% RH, and then measured for the amount of electric charge by means of a Farady gauge, exhibiting only 1/15 to 1/30 of the initial amount of charge after 10 minutes' interval. Meanwhile, a similar test employing the usually available polymethylmethacrylate plates revealed retention of 2/3 of the original quantity of electricity after 10 minutes' interval. Thus, this molded body exhibited outstanding antistatic property.

EXAMPLE 8

25.2 g of N-(6-amino-n-hexyl)δ-amino-n-butanesulfonic acid lithium salt, 320 g of ω,ω'-di-(aminotolylcarbamoyl) polytetramethylene glycol (amine value 35.1), 19.8 g of 4,4'-diphenylmethanediamine, 0.900 g of distilled water, and 371 g of silica powder were placed in a 2 l beaker, heated to 80° to 100° C. for fusion-mixing, and then cooled to 60° C. Thereafter, 2.10 g of triethylenediamine, 0.400 g of stannous octoate, and 60.9 g of tolylenediisocyanate (2,4-tolylenediisocyanate:2,6-tolylenediisocyanate=80:20) were added to the cooled mixture and again fully mixed. Subsequently, the mixture was poured into a 2 l paper container, and heated at the room temperature for 1 hour, then at 80° C. for 2 hours, and finally at 120° C. for additional 1 hour, and thus there was obtained a molded product. The composition of this molded product was obtained from the sulfonate equivalent and the elementary analysis value of nitrogen found by means of titration (x=0.316, y=0.655, z=0.0286). This sample was cut out into a plate with dimensions of 5.0×5.0×0.5 cm, which was subjected to 5 seconds' application of 10 KV voltage at a distance of 3.5 cm for charging at a level of 3 to 5×10⁻¹⁰ C/cm², left in an atmosphere at 20° C. and 40% to 65% RH, and then measured for the amount of electric charge by means of the Farady gauge, exhibiting zero level after 20 minutes' interval. Thus, this molded body exhibited outstanding antistatic property.

EXAMPLE 9

Employing the same devices as those of Example 1, 90 ml of dimethylsulfoxide, 3.66 g of N-(6-amino-n-hexyl)γ-amino-n-propanesulfonic acid lithium salt, 0.90 g of ethylenediamine, and 0.112 g of dibutyltindilaurate were placed in the flask, subjected to nitrogen-substitution, and stirred while keeping the flask at 27° C. A solution of 7.51 g of 4,4'-diphenylmethanediisocyanate in 10 ml of dimethylsulfoxide was dropped stepwise into the stirred mixture through the dropping funnel for 10 minutes. After completion of such dropping, the mixture was kept under stirring for the further 4 hours, and then the liquid temperature was raised to 61° C. for additional 2 hours' polymerization. While being stirred continuously, the reaction mixture was added to a large excess amount of acetonitrile, and thus there was obtained a colorless, powdered polymer (yield 8.39 g, yield rate 69.5%, softening point 32° to 35° C., η30° C. inh/DMSO=0.406). From the infrared absorption spectrum and nuclear magnetic resonance spectrum, this polymer was found to be a sulfonate polyurea composed of x- and y-units.

What we claim is:

1. A urea compound having sulfonate radical, represented by the general formula:

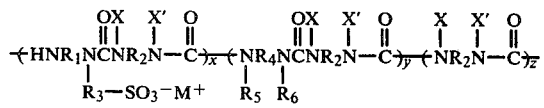

where R₁ is a divalent hydrocarbon-based radical having 2 to 17 carbon atoms, R₂ is a divalent hydrocarbon-based radical having 4 to 29 carbon atoms or polyether or polyester having an average molecular weight of 10,000 or less, R₃ is $$\begin{array}{cccc} R_\delta & R_\gamma & R_\beta & R_\alpha \\ | & | & | & | \\ -C-C-\!\!\!-C-\!\!\!-C\text{-radical}, \\ | & | & | & | \\ H & R_{\gamma'} & R_{\beta'} & R_{\alpha'} \end{array} \qquad \begin{array}{ccc} R_\gamma & R_\beta & R_\alpha \\ | & | & | \\ -C-C-\!\!\!-C\text{-radical} \\ | & | & | \\ H & R_{\beta'} & R_{\alpha'} \end{array}$$

(wherein $R\alpha$; $R\alpha'$; $R\beta$; $R\beta'$; $R\gamma$; $R\gamma'$ and $R\alpha$ are independently hydrogen, alkyl radicals having 1 to 5 carbon atoms or monovalent radicals excluding hydrogen and alkyl radicals), $R_4$ is a divalent hydrocarbon-based radical having 2 to 17 carbon atoms, $R_5$ and $R_6$ are independently a monovalent hydrocarbon-based radical having 1 to 16 carbon atoms or a divalent hydrocarbon-based radical to form together by mutual bond a carbon chain, X and X' are hydrogen or a biuret bridge, M+ is a cation, and x, y and z are values indicating the relative molar proportions of the respective units and complying with the required normalization: $x+y+z=1$; $0.1 < 100x/(x+y+z) < 100$; and $0 < 100z/x+y+z < 50$.

2. A urea compound according to claim 1, wherein said y and z are each zero, and which is represented by the formula:

$$\begin{array}{c} \text{OX} \quad \text{X'} \quad \text{O} \\ \| \| \quad | \quad \| \\ -\!\!(\text{HNR}_1\text{NCNR}_2\text{N}-\text{C})_{\!\!\overline{x}}- \\ | \\ R_3-\text{SO}_3-\text{M}^+ \end{array}$$

where $R_1$, $R_2$, $R_3$, X, X' and M+ are as defined above.

3. A urea compound according to claim 1, wherein said z is zero, and which is represented by the formula:

$$\begin{array}{cc} \text{OX} \quad \text{X'} \quad \text{O} & \text{OX} \quad \text{X'} \quad \text{O} \\ \| \| \quad | \quad \| & \| \| \quad | \quad \| \\ -\!\!(\text{HNR}_1\text{NCNR}_2\text{N}-\text{C})_{\!\!\overline{x}}\!\!-\!\!(\text{NR}_4\text{NCNR}_2\text{N}-\text{C})_{\!\!\overline{y}}\!\!- \\ | & | \quad | \\ R_3-\text{SO}_3-\text{M}^+ & R_5 \quad R_6 \end{array}$$

where $R_1$, $R_2$, $R_3$, $R_4$, $R_5$, $R_6$, X, X' and M+ are as defined above, and x and y indicate the relative molar proportions of the respective corresponding units and comply with the required normalization: $x+y=1$ and $0.1 < 100x/(x+y) < 100$.

4. A urea compound according to claim 1, wherein said y is zero, and which is represented by the formula:

$$\begin{array}{cc} \text{OX} \quad \text{X'} \quad \text{O} & \text{X} \quad \text{X'} \quad \text{O} \\ \| \| \quad | \quad \| & | \quad | \quad \| \\ -\!\!(\text{HNR}_1\text{NCNR}_2\text{N}-\text{C})_{\!\!\overline{x}}\!\!-\!\!(\text{NR}_2\text{N}-\text{C})_{\!\!\overline{z}}\!\!- \\ | \\ R_3-\text{SO}_3-\text{M}^+ \end{array}$$

where $R_1$, $R_2$, $R_3$, X, X' and M+ are as defined above, and x and z indicate the relative molar proportions of the respective corresponding unit and comply with the required normalization: $x+z=1$ and $0 < 100z < 50$.

5. A urea compound according to claim 1, wherein said x, y and z are each more than zero, and which is represented by the formula:

$$\begin{array}{ccc} \text{OX} \quad \text{X'} \quad \text{O} & \text{OX} \quad \text{X'} \quad \text{O} & \text{X} \quad \text{X'} \quad \text{O} \\ \| \| \quad | \quad \| & \| \| \quad | \quad \| & | \quad | \quad \| \\ -\!\!(\text{HNR}_1\text{NCNR}_2\text{N}-\text{C})_{\!\!\overline{x}}\!\!-\!\!(\text{NR}_4\text{NCNR}_2\text{N}-\text{C})_{\!\!\overline{y}}\!\!-\!\!(\text{NR}_2\text{N}-\text{C})_{\!\!\overline{z}}\!\!- \\ | & | \quad | \\ R_3-\text{SO}_3-\text{M}^+ & R_5 \quad R_6 \end{array}$$

where $R_1$, $R_2$, $R_3$, $R_4$, $R_5$, $R_6$, X, X' and M+ are as defined above, and x, y and z indicate the relative molar proportions of the respective corresponding units and comply with the required normalization: $x+y+z=1$ and $0.1 \leq 100x/(x+y+z) < 100$.

6. A urea compound according to claim 1, wherein the molar ratio of the $$\begin{array}{c} \text{O} \\ \| \\ -\text{C}-\text{NH}- \end{array}$$

radical occupies 30% or less of the total molar amounts of X and X' radicals.

7. A urea compound according to claim 1, wherein said $R_1$ is a radical selected from the group consisting of aliphatic hydrocarbon radicals having 2 to 17 carbon atoms; alicyclic, aliphatic-substituted alicyclic, aromatic, aliphatic-substituted aromatic, alicyclic-substituted aromatic and aliphatic-substituted alicyclic-substituted aromatic hydrocarbon radicals having 6 to 15 carbon atoms; derivatives thereof substituted with halogen; and oxadialkylene radicals having 2 to 17 carbon atoms.

8. A urea compound according to claim 7, wherein said $R_1$ is selected from the group consisting of hexamethylene, p-phenylene.

9. A urea compound according to claim 1, wherein said $R_2$ is a radical selected from the group consisting of aliphatic hydrocarbon radicals having 4 to 16 carbon atoms, alicyclic hydrocarbon radicals having 8 to 20 carbon atoms, aliphatic-substituted aromatic hydrocarbon radicals having 9 to 20 carbon atoms, alicyclic-substituted aromatic hydrocarbon radicals having 12 to 20 carbon atoms and aromatic hydrocarbon radicals having 8 to 29 carbon atoms.

10. A urea compound according to claim 9, wherein said $R_2$ is hexamethylene, 4,4-diphenylmethane, 2,4-tolylene or 2,6-tolylene radical.

11. A urea compound according to claim 1, wherein said M is one member selected from alkaline metals, alkaline earth metals and tertiary amines.

12. A urea compound according to claim 1, wherein $R_5$ and $R_6$ are independently hydrogen atom, aliphatic hydrocarbon radicals having one to 16 carbon atoms, alicyclic, aliphatic-substituted alicyclic, aromatic, aliphatic-substituted aromatic, alicyclic-substituted aromatic, or aliphatic-substituted alicyclic-substituted aromatic hydrocarbon having 3 to 13 carbon atoms.

13. A urea compound according to claim 1, $R_4$ is ethylene or diphenylmethane, and $R_5$ and $R_6$ are hydrogen atoms.

14. A method for producing a urea compound having sulfonate radical and represented by the formula:

$$\begin{array}{ccc} \text{X} \quad \text{X'} \quad \text{O} & \text{OX} \quad \text{X'} \quad \text{O} & \text{X} \quad \text{X'} \quad \text{O} \\ | \quad | \quad \| & \| \| \quad | \quad \| & | \quad | \quad \| \\ -\!\!(\text{HNR}_1\text{NCNR}_2\text{N}-\text{C})_{\!\!\overline{x}}\!\!-\!\!(\text{NR}_4\text{NCNR}_2\text{N}-\text{C})_{\!\!\overline{y}}\!\!-\!\!(\text{NR}_2\text{N}-\text{C})_{\!\!\overline{z}}\!\!- \\ | & | \quad | \\ R_3-\text{SO}-\text{M}^+ & R_5 \quad R_6 \end{array}$$

which method comprises reacting an aminoaminosulfonic acid salt represented by the formula:

$$\begin{array}{c} \text{H}_2\text{NR}_1\text{NH} \\ | \\ R_3-\text{SO}_3-\text{M}^+ \end{array}$$

with a diisocyanate represented by the formula:

OCNR$_2$NCO, optionally in the presence of water and/or a diamine represented by the formula:

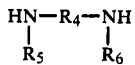

where $R_1$ is a divalent hydrocarbon-based radical having 2 to 17 carbon atoms, $R_2$ is a divalent hydrocarbon-based radical having 4 to 29 carbon atoms or polyether or polyester having an average molecular weight of 10,000 or less, $R_3$ is

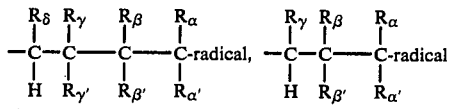

(wherein $R\alpha, R\alpha'$; $R\beta$; $R\beta'$; $R\gamma$; $R\gamma'$ and $R\alpha$ are independently hydrogen, alkyl radicals having 1 to 5 carbon atoms or monovalent radicals excluding hydrogen and alkyl radicals), $R_4$ is a divalent hydrocarbon-based radical having 2 to 17 carbon atoms, $R_5$ and $R_6$ are independently a monovalent hydrocarbon-based radical having 1 to 16 carbon atoms or a divalent hydrocarbon-based radical to form together by mutual bond a carbon chain, X and X' are hydrogen or a biuret bridge, M+ is a cation, and x, y and z are values indicating the relative molar proportions of the respective units and complying with the required normalization: $x+y+z=1$, $0.1 \leq 100x/(x+y+z) \leq 100$; and $0 \leq 100z/x+y+z \leq 50$.

15. A method according to claim 14, wherein only the aminoaminosulfonic acid salt and the diisocyanate are the indispensable reactants, and which produces a urea compound represented by the formula:

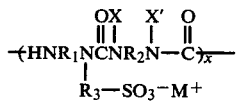

where $R_1$, $R_2$, $R_3$, X, X' and M+ are as defined above.

16. A method according to claim 14, wherein the aminoaminosulfonic acid salt, the diisocyanate and the diamine are the indispensable reactants, and which produces a urea compound represented by the formula:

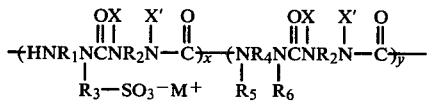

where $R_1$, $R_2$, $R_3$, $R_4$, $R_5$, $R_6$, X, X' and M+ are as defined above, and x and y indicate the relative molar proportions of the respective corresponding units and comply with the required normalization: $x+y=1$ and $0.1 \leq 100x/(x+y) < 100$.

17. A method according to claim 14, wherein the aminoaminosulfonic acid salt, the diisocyanate and the water are indispensable reactants, and which produces a urea compound represented by the formula:

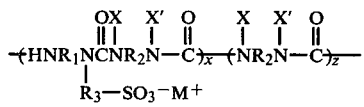

where $R_1$, $R_2$, $R_3$, X, X' and M+ are as defined above, and x and z indicate the relative molar proportions of the respective corresponding units and comply with the required normalization: $x+z=1$ and $0 < 100z < 50$.

18. A method according to claim 14, wherein all the aminoaminosulfonic acid salt, the diisocyanate, the diamine and the water are indispensable reactants, and which produces a urea compound represented by the formula:

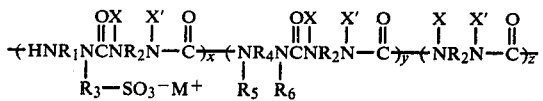

where $R_1$, $R_2$, $R_3$, $R_4$, $R_5$, $R_6$, X, X' and M+ are as defined above, and x, y and z indicate the relative molar proportions of the respective corresponding units and comply with the required normalization: $x+y+z=1$ and $0.1 \leq 100x/(x+y+z) < 100$.

19. A method according to claim 14, wherein said reaction is an interfacial polymerization.

20. A method according to claim 19, wherein water is used as a solvent for the aminoaminosulfonic acid salt, and a water-insoluble organic solvent which does not react with the aminoaminosulfonic acid salt and the diisocyanate is used as a solvent for the diisocyanate.

21. A method according to claim 19, wherein said organic solvent is carbon tetrachloride.

22. A method according to claim 19, wherein said aminoaminosulfonic acid salt is prepared by the addition of the base M to the corresponding aminoaminosulfonic acid before the polymerization.

23. A method according to claim 19, wherein the reaction is performed through a first step wherein the reaction is carried out at a relatively low temperature and in the absence of a catalyst, a second step wherein the reaction is carried out in the presence of a catalyst, a third step wherein the reaction is carried out at a relatively high temperature or a combination of these steps.

24. A method according to claim 23, wherein in subsequent to the completion of most of the polymerization reaction, the temperature is raised 5° to 30° C. higher than the previous reaction temperature for attaining a further completion of the polymerization reaction.

25. A method according to claim 20, wherein the concentration of each of the reactants in each of the solvents is 0.1 to 40% by weight.

26. A method according to claim 20, wherein the concentration of each of the reactants in each of the solvents is 1% to 30% by weight.

27. A method according to claim 20, wherein the reaction is carried out at a temperature of more than a freezing point of the reaction system up to less than 100° C.

28. A method according to claim 27, wherein the reaction is carried out at a temperature of less than a boiling point of the organic solvent.

29. A method according to claim 20, wherein the reaction is carried out at a temperature of 0° C. to 60° C.

30. A method according to claim 20, wherein the reaction is carried out at a temperature of 0° C. to 35° C.

31. A method according to claim 14, wherein the reaction is a solution polymerization.

32. A method according to claim 31, wherein a polar aprotic solvent is used.

33. A method according to claim 32, wherein the polar aprotic solvent is selected from the group consisting of tertiary amides, aprotic organic sulfur oxides and triesters of phosphoric acid.

34. A method according to claim 32, wherein an electrolyte which does not react with the diisocyanate, the aminoaminosulfonic acid salt and the polar aprotic solvent is added as a solubilizing agent.

35. A method according to claim 32, wherein the corresponding aminoaminosulfonic acid and the base M are added to the polar aprotic solvent to neutralize, thereby forming a solution of the aminoaminosulfonic acid salt.

36. A method according to claim 35, wherein a neutral dehydrating agent is added so as to remove water produced during the neutralization.

37. A method according to claim 32, wherein a solution of the diisocyanate is slowly added to a solution of the aminoaminosulfonic acid salt.

38. A method according to claim 31, wherein the reaction is conducted under an inert atmosphere.

39. A method according to claim 31, wherein the reaction is performed at a temperature of more than a freezing point of the reaction system up to 200° C.

40. A method according to claim 39, wherein the reaction is performed at a temperature of more than a freezing point of the reaction system up to 100° C.

41. A method according to claim 31, wherein the reaction is performed through a first step wherein the reaction is carried out at a relatively low temperature and in the absence of a catalyst, a second step wherein the reaction is carried out in the presence of a catalyst, a third step wherein the reaction is carried out at a relatively high temperature or a combination of these steps.

42. A method according to claim 40, wherein the reaction is carried out by effecting the first or second step to complete most of the reaction and subsequently conducting the third step at a temperature 5° C. to 100° C. higher than the temperature at which the first or second step is effected to finally complete the reaction.

43. A method according to claim 31, wherein the concentration of each of the reactants in each of the solvents is 1% to 50% by weight.

44. A method according to claim 31, wherein the concentration of each of the reactants in each of the solvents is 5% to 30% by weight.

45. A method according to claim 14, wherein the reaction is a solvent-free polymerization.

46. A method according to claim 45, wherein the reactants are mixed, charged in a container or a casting mold and reacted there.

47. A method according to claim 45, wherein the reaction is carried out through a first step wherein the reaction is conducted at a relatively low temperature and in the absence of a catalyst, a second step wherein the reaction is conducted in the presence of a catalyst or a combination of these steps.

48. A method according to claim 47, wherein the reaction is carried out through the two steps, and the first step is carried out at a temperature of 0° C. to 100° C. and the second step is effected at a temperature higher than that of the first step.

49. A method according to claim 47, wherein the second step is effected at a temperature of 50° C. to 200° C.

50. A method according to claim 45, wherein a diluent filler is added.

51. A method according to claim 50, wherein the diluent filler is silica powder.

* * * * *